United States Patent [19]

Nakamura et al.

[11] Patent Number: 5,724,980
[45] Date of Patent: Mar. 10, 1998

[54] PULSE DIAGNOSIS METER

[76] Inventors: Yoshinobu Nakamura, 18-3, Yoneyama 4-chome, Niigata-shi, Niigata-ken; Kiyoharu Nakamura, 3295, Oaza-Nishidani, Koshiji-machi Santo-gun, Niigata-ken, both of Japan

[21] Appl. No.: 725,667

[22] Filed: Oct. 1, 1996

[30] Foreign Application Priority Data

Jan. 19, 1996 [JP] Japan .................................. 8-025975

[51] Int. Cl.$^6$ ......................................................... A61B 5/02
[52] U.S. Cl. ................................................................. 128/679
[58] Field of Search ........................... 128/677, 679-683

[56] References Cited

U.S. PATENT DOCUMENTS

| | | | |
|---|---|---|---|
| 4,651,748 | 3/1987 | Vinogradov et al. | 128/682 |
| 4,718,426 | 1/1988 | Russell | 128/679 |
| 5,050,613 | 9/1991 | Newman et al. | 128/679 |
| 5,316,005 | 5/1994 | Tomita | 128/680 |

FOREIGN PATENT DOCUMENTS 6-3529  1/1991  Japan.

*Primary Examiner*—William E. Kamm
*Assistant Examiner*—George R. Evanisko
*Attorney, Agent, or Firm*—Pollock, Vande Sande & Priddy

[57] ABSTRACT

A pulse diagnosis meter is provided to suitably carry out diagnosis and medicare in the case where the blood pressure and pulse pressure are imbalanced. Two blood pressure sensors having the same structure are provided for measuring simultaneously the blood pressure and the pulse pressure on the right and left side arms of a person to be examined. A processor is provided for affecting predetermined calculations. A display indicates the calculation result. It is possible to immediately know the state of the pulse pressure and the balance of the blood pressure values on the right and left, which would be likely to overlook only by the measurement of the blood pressure of one arm of the person to be examined.

8 Claims, 1 Drawing Sheet

PULSE DIAGNOSIS METER

BACKGROUND OF THE INVENTION

1. Field of the Invention

The present invention relates to a pulse diagnosis meter for measuring right and left blood pressures of the human body and for displaying a difference between the right and left blood pressures for various diagnoses.

2. Description of the Related Art

In a conventional pulse diagnosis meter, it is known that a pressure value of a cuff band, a maximum blood pressure (contraction blood pressure) on the basis of an input signal from a sound sensor and a minimum blood pressure (relaxation blood pressure) are calculated or displayed in combination of the cuff band and Korotkoff sound sensor, and a predetermined blood pressure value is detected, calculated and displayed the basis of a pressure of the cuff band and a volume change (pressure change) of the cuff band pressure gas during the measurement.

However, in the case where the blood pressures are measured on the right and left arms of the human body, there are some cases that the blood pressures are different between right arid left. This results from an imbalance of the autonomic nervous system on the right and left of the human body. In this connection, Japanese Utility Model Publication No. Hei 6-3529 proposes an automomic nervous system balance meter for simultaneously measuring the blood pressures on the right arid left arms and for indicating the result.

However, in the conventional blood pressure measurement, the measurement is carried out only on one arm of the human body for the diagnosis.

However, in the case where the results on the right and left measurements are remarkably different from each other, there is a fear that the diagnosis would be adversely affected. For example, if the lower blood pressure would be measured and the diagnosis would be made as a normal value, there would be a possibility to overlook the high blood pressure. Inversely, the high blood pressure would be measured and diagnosis would be made for giving a hypotensive to the human body, the blood supply amount to the artery on the bottom of the brain would be insufficient to be likely to cause a cerebral infarction. This may be confirmed by an X-ray photograph through a vertebra artery angiograph of the person who suffers from the difference in blood pressure on the right and left, so that the blood supply from the vertebra artery on one side is prevented.

Also, touching diagnosis of pulses is well known as the diagnosing means. However, the touching diagnosis of the pulses needs a large amount of experience.

SUMMARY OF THE INVENTION

Accordingly, an object of the present invention is to provide a novel pulse diagnosis meter which prevent a potential cerebral infarction, which may display the pulse numbers corresponding to the pulse diagnosis and which may readily recognize danger factors.

According to the present invention, there is provided a sphygmomanometer comprising:

a blood pressure sensor section having two sensors having the same structure;

a processor section having functions for detecting two kinds of contraction blood pressures and relaxation blood pressures in accordance with signals from each of the sensor, respectively, calculating a differential value of two kinds of the contraction blood pressure values, a differential value of two kinds of the relaxation blood pressure values, two kinds of pulse pressures which are differences between the contraction blood pressure values and the relaxation blood pressure values, and a differential value of the two kind of pulse pressures, and judging whether or not the differential values are equal to or more than predetermined values, respectively; and a display section for displaying the detected data and the calculated data, and the judgement results.

Namely, the contraction blood pressure values (A1, B1) detected by the right and left sensors and the relaxation blood pressure values (A2, B2) are displayed. The difference values (C1=|A1-|, C2=|A2-B2|) between the contraction blood pressure values and the relaxation blood pressure values are calculated, and the results are displayed. A warning is displayed in the case where the difference values C1 are equal to or more than a predetermined level. Also, pulse pressure values (Da=|A1-A2|, Db=|B1-B2|) are calculated and displayed. Furthermore, the pulse pressure difference value (D=|Da-Db|) is calculated and displayed.

Accordingly, the blood pressure values are displayed and the blood pressure differential values are displayed. Accordingly, it is possible to know immediately the blood pressure balance on the right and left. It is possible to confirm the danger of generation of the cerebral infarction by the abnormal balance and it is possible to effect the suitable diagnosis.

Also, knowing the pulse pressure values and the pulse pressure differential values leads to a numerically knowing the diagnosis causes for the pulse examination which is popular in the Oriental medical science.

DESCRIPTION OF THE PREFERRED EMBODIMENTS

Figure 1:
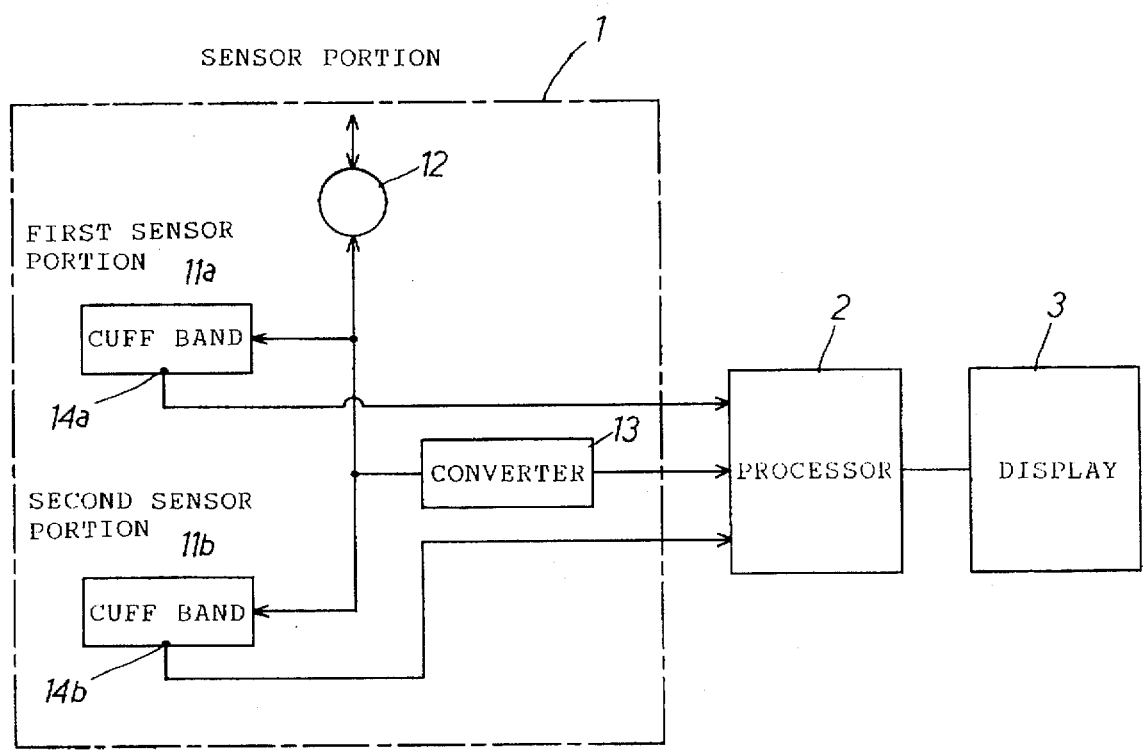
FIG. 1 is a simple block diagram showing an embodiment of the invention.

An embodiment of the present invention will now be described with reference to the accompanying drawings.

A pulse diagnosis meter in accordance with the embodiment is provided with a sensor section 1, a processor section 2 and a display section 3. The sensor section 1 is provided with well known blood pressure detecting functions. The sensor section 1 has a first sensor 11a and a second sensor 11b each of which is composed of a cuff band to be wound around the right and left arms. The sensor section 1 is provided with a pump 12 for supplying air to the cuff bands and evacuating the air from the cuff band for controlling the air pressures within the cuff bands, and a converter 13 for converting the air pressure values of the cuff bands into electric signals. Furthermore, Korotkoff sound sensors 14a and 14b made by microphones are provided on the cuff bands, respectively.

The processor section 2 is composed of a micro computer installed with a predetermined program for recognizing the electric signals into which the sounds are converted from the Korotkoff sound sensors 14a and 14, detecting two kinds of contraction blood pressure value (A1, B1) and relaxation blood pressure value (A2, B2) on the basis of the pressure values within the cuff bands at the start of the sounds and the end of the sound and for calculating the differential value between the contraction blood pressure values (C1=|A1−B1|), the differential value between the relaxation blood pressure values ($C2=|A2-B2|$), two kinds of pulse pressure values ($Da=|A1-A2|$, $Db=|B1-B2|$) which are differences between the contraction blood pressure values and relaxation blood pressure values, and the pulse pressure differential value ($D=|Da-Db|$), respectively, on the basis of these detected data. Also, the processor section is particularly provided with a judgement function for judging whether or not the contraction blood pressure differential value C1 is equal to or more than a predetermined value.

The display section 3 uses a suitable liquid crystal digital display for displaying the detected values A1, A2, B1 and B2 and the calculated difference values C1 and C2, the pulse pressure values Da and Db and the pulse pressure differential value D and further displaying a warning in the case here the differential value C1 is equal to or more than a predetermined value by the judgement function. The display section 3 may be provided with a printing function for printing out various values as desired.

The respective cuff bands (sensors) 11a and 11b reloaded on the right and left arms of the person to be examined. In the same manner as in the conventional blood pressure measurement, the pump 12 of the sensor section 1 is driven, and the air pressure of the cuff bands 11a and 11b are gradually decreased from a constant level for a predetermined measurement. The each blood pressure values and the calculated values are blood pressure values A1, A2, B1 and B2, measured simultaneously on the right and left arms of the person to be examined, the right and left blood pressure differential values C1, C2, the right and left pulse pressures Da, Db and the pulse pressure differential value D.

Accordingly, the blood pressure which is higher in blood pressure value on the right and left sides may be used as a reference blood pressure for the brain, and the lower blood pressure may be used as an index representative of the insufficiency of the blood to the brain, so that a suitable diagnosis may be carried out. In particular, the differential values C1, C2 are used of the judgement index of the dangerous factor of the blood pressure. In particular, the angiography is not necessary and the blood flow state from the vertebra artery to the artery on the bottom of the brain may be inferred. It is possible to prevent the generation of the cerebral infarction or the like by the quick warning.

Also, according to the numerical representation of the pulse pressure, it is possible to easily find out the abnormality in view of the blood pressure, to numerically see the state of the patient such as an inflammation or a strength of a pain, and also to judge whether a suitable diagnosis for, for example, the precaution of the hemiparaplegia or palsy is based upon the right or left blood pressure of the patient.

In the case where the pulse diagnosis meter is specialized for checking out the blood flow to the brainstem portion or the pulse pressure, it is only necessary to display the limited numerical values. Also, with respect to the measurement of the blood pressure, the invention is not limited to the above-described embodiment but may be applied to any diagnosis if the measurement and detection are simultaneously carried out under the same conditions for the right and left arms.

Furthermore, if the pulse sounds from the Korotkoff sound sensors 14a and 14b are converted into the electric signals for the processor section 2, the pulse sounds are analyzed (judgement for the high sound or low sound and the strength of the sounds) on the basis of the electric signals, CRT is adopted to the display section 3 and the pulse sounds are represented visually, as desired, it is possible to effect more positive pulse examination.

As described above, according to the present invention, there are provided the two blood pressure sensors having the same structure, and both the right and left arms of the person to be examined may be simultaneously measured. After the predetermined calculations and the display of the balance of the right and left blood pressures obtained by the calculation results and the right and left pulse pressure values, the state of the pulse pressure, the balance of the right and left blood pressures which is likely to overlook when the diagnosis is carried out only with one arm of the person to be examined may be immediately known. It is thus possible to effect the suitable diagnosis with the instrument according to the present invention.

Various details of the invention may be changed without departing from its spirit nor its scope. Furthermore, the foregoing description of the embodiments according to the present invention is provided for the purpose of illustration only, and not for the purpose of limiting the invention as defined by the appended claims and their equivalents.

What we claim is:

1. A pulse diagnosis meter comprising:
    a blood pressure sensor section having two sensors with similar structure, each sensor producing pressure signals;
    a processor section, including processor means for simultaneously detecting contraction blood pressures in accordance with said pressure signals from each of the sensors, respectively, for calculating a difference between the contraction blood pressures from each of the sensors, and for determining whether or not the difference is equal to or greater than a predetermined value; and
    a display section, including display means for displaying the detected blood pressures, the difference value and a representation of the determination.

2. A pulse diagnosis meter comprising:
    a blood pressure sensor section having two sensors, each with similar structure, said sensors including a right sensor adapted for mounting on a right arm, and a left sensor adapted for mounting on a left arm, respectively; each sensor producing pressure signals;
    a processor section, including processor means for simultaneously detecting contraction blood pressures in accordance with said pressure signals from each of the sensors, respectively, for calculating a difference between the contraction blood pressures from each of the sensors, and for determingin whether or not the difference is equal to or greater than a predetermined value; and
    a display section, including display means for displaying the detected blood pressures, the difference value and a representation of the determination.

3. A pulse diagnosis meter comprising:
    a blood pressure sensor section having two sensors with similar structure, each sensor producing pressure signals;
    a processor section including processor means for simultaneously detecting relaxation blood pressures in accordance with said pressure signals from each of the sensors, respectively, for calculating a difference between the relaxation blood pressures and for determining whether or not said difference is equal to or greater than a predetermined value; and
    a display section, including display means for displaying the detected blood pressures, the difference value and a representation of the determination.

4. A pulse diagnosis meter comprising:

a blood pressure sensor section having two sensors, each with similar structure, said sensors including a right sensor adapted for mounting on a right arm, and a left sensor adapted for mounting on a left arm, respectively; each sensor producing pressure signals;

a processor section, including processor means for simultaneously detecting relaxation blood pressures in accordance with said pressure signals from each of the sensors, respectively, for calculating a difference between the relaxation blood pressures from each of the sensors, and for determining whether or not the difference is equal to or greater than a predetermined value; and a display section, including display means for displaying the detected blood pressures, the difference value and a representation of the determination.

5. A pulse diagnosis meter comprising:

a blood pressure sensor section having two sensors with similar structure, each sensor producing pressure signals;

a processor section including processor means for simultaneously detecting contraction blood pressures from each of the sensors and for simultaneously detecting relaxation blood pressures from each of the sensors, all of said detecting occurring in accordance with said pressure signals from the sensors, respectively, for calculating first and second pressure differences between contraction blood pressures and relaxation blood pressures, respectively, for further calculating a third pressure difference between said first and second pressure difference and for determining whether or not the first or second pressure difference or the third pressure difference is equal to or greater than predetermined values, respectively; and a display section including display means for displaying the respective pressures, the first and second and third pressure difference, and a representation of the determination.

6. A pulse diagnosis meter comprising:

a blood pressure sensor section having two sensors, each with similar structure, said sensors including a right sensor adapted for mounting on a right arm, and a left sensor adapted for mounting on a left arm, respectively; each sensor producing pressure signals;

a processor section including processor means for simultaneously detecting contraction blood pressures from each of the sensors and for simultaneously detecting relaxation blood pressures from each of the sensors, all of said detecting occurring in accordance with said pressure signals from the sensors, respectively, for calculating first and second pressure differences between contraction blood pressures and relaxation blood pressures, respectively, for further calculating a third pressure difference between said first and second pressure difference and for determining whether or not the first or second pressure difference or the third pressure difference is equal to or greater than predetermined values, respectively; and a display section including dispaly means for displaying the respective pressures, the first and second and third pressure difference, and a representation of the determination.

7. A pulse diagnosis meter comprising:

a blood pressure sensor section with two sensors each having substantially the same structure and producing pressure signals;

a processor section including processor means for simultaneously detecting contraction blood pressures and for simultaneously detecting relaxation blood pressure from each of the sensors, all of said detecting occurring in accordance with said pressure signals, respectively for calculating a difference between the contraction blood pressure, a difference between the relaxation blood pressure for each of the sensors for calculating first and second pressure difference between contraction and relaxation blood pressures respectively and a third difference between the first and second pressure differences, respectively, and for determining whether or not said differences are equal to or greater than predetermined values, respectively; and a display section including display means for displaying the pressures, the difference values, and a representation of the determination.

8. A pulse diagnosis meter comprising:

a blood pressure sensor section having two sensors, each with similar structure, said sensors including a right sensor adapted for mounting on a right arm, and a left sensor adapted for mounting on a left arm, respectively;

a processor section, including processor means for simultaneously detecting contraction blood pressures and relaxation blood pressures from said right and left sensors in accordance with said pressure signals from each of the sensors, respectively, for calculating a difference between the contraction blood pressures from each of the sensors, a difference between the relaxation blood pressures for each of the sensors, for calculating first anal second pressure differences between contraction and relaxation blood pressures and a third difference between the first and second differences, respectively, and for determining whether or not differences are equal to or greater than predetermined values; and a display section, including display means for displaying the detected blood pressures, the difference value and a representation of the determination.

* * * * *

UNITED STATES PATENT AND TRADEMARK OFFICE
CERTIFICATE OF CORRECTION

PATENT NO. : 5,724,980
DATED : March 10, 1998
INVENTOR(S) : Nakamura et al

It is certified that error appears in the above-identified patent and that said Letters Patent is hereby corrected as shown below:

Abstract, line 7, change "affecting" to --effecting--.

Col. 1, line 18, after "displayed" insert --on--.

Col. 1, line 24, change "arid" to --and--.

Col. 1, line 27, change "automomic" to --autonomic--.

Col. 2, line 15, change "(C1= |A1-|, C2= |A2-B2|)" to --(C1= |A1-B1|, C2= |A2-B2|)--.

Col. 6, line 45, change "anal" to --and--.

Signed and Sealed this

Twenty-first Day of March, 2000

Attest:

Attesting Officer

Q. TODD DICKINSON

Commissioner of Patents and Trademarks